United States Patent [19]

Charlton et al.

[11] 4,133,951

[45] Jan. 9, 1979

[54] VITAMIN B-12 COBALT-57 AND PROCESS

[75] Inventors: John C. Charlton; Alan L. Hamilton, both of Amersham, England

[73] Assignee: The Radiochemical Centre Limited, England

[21] Appl. No.: 667,619

[22] Filed: Mar. 17, 1976

Related U.S. Application Data

[63] Continuation of Ser. No. 576,361, May 8, 1975, abandoned.

[51] Int. Cl.$^2$ .................. A61K 31/68; C07H 23/00
[52] U.S. Cl. ........................... 536/25; 424/1.5; 424/201
[58] Field of Search ............................ 536/25

[56] References Cited

U.S. PATENT DOCUMENTS

| 3,115,489 | 12/1963 | Cords et al. | 536/25 |
| 3,798,211 | 3/1974 | Mervyn | 536/25 |
| 3,936,440 | 2/1976 | Nath | 536/25 |

OTHER PUBLICATIONS

"British Pharmacopeia," 1973, pp. 131, 132.
"United States Pharmacopeia XIX," 1975, pp. 111–112.
Koppenhagen, et al., "Jour. Biol. Chem.", vol. 246, 1971, pp. 3075–3077.
Koppenhagen, et al., "Jour. Biol. Chem.", vol. 248, 1973, pp. 7999–8002.
Toohey, "Proceedings National Acad. of Science", vol. 54, 1965, pp. 934–942.

Primary Examiner—Johnnie R. Brown
Attorney, Agent, or Firm—Wenderoth, Lind & Ponack

[57] ABSTRACT

A method of making radioactively labelled vitamin B-12 by reacting α-(5,6-dimethylbenzimidazolyl)hydrogenobamide with cobaltous ion Co-57, or with another radioactive cobalt isotope. The method enables vitamin B-12 of high specific activity to be made, which is useful for in vitro and in vivo analysis.

6 Claims, No Drawings

VITAMIN B-12 COBALT-57 AND PROCESS

This is a continuation of Ser. No. 576,361, filed May 8, 1975, now abandoned.

vitamin B-12, was first isolated in 1948. It is extensively employed in the treatment of vitamin B-12 deficiency states, notably pernicious anaemia.

This application concerns the manufacture of radioactive forms of vitamin B-12 in which the cobalt atom present in the vitamin B-12 molecule is replaced with a radioactive isotope of cobalt, usually cobalt-57 or cobalt -58. Such radioactive forms of vitamin B-12 are used extensively in the diagnosis of vitamin B-12 deficiency states, using both in vivo techniques (in which labelled vitamin B-12 is administered to the patient) and in vitro techniques in which the labelled vitamin B-12 is used as a laboratory agent in the examination of samples of the patient's serum.

Vitamin B-12 labelled with a radioactive isotope of cobalt, namely cobalt-60, was first described in 1950 (Chaiet, L, Rosenblum, C and Woodbury, D T, Science, 1950, 111, 601-602). The test for vitamin B-12 adsorption used currently in the diagnosis of vitamin B-12 deficiency states is based upon that described by Schilling in 1953 (Schilling, R F, J Lab Clin Med, 1953, 42,860-866). The determination of the levels of vitamin B-12 in blood, employing radioactive vitamin B-12 as a laboratory agent, was first described by Ekins in 1961, (Barakat, R M and Ekins, R P, Lancet, 1961, Part 2, 25-26).

Radioactive forms of vitamin B-12, for use in the diagnostic procedures described above, have been available commercially for about 20 years. Their preparation has employed the basic method used in the commercial production of non-radioactive vitamin B-12, namely, the growth of a suitable mould, for example, streptomyces griseus, on a medium containing suitable nutrients together with a radioactive isotope of cobalt (nowdays either cobalt-57 or cobalt-58) in the form of cobaltous ion.

As compared with the preparation of inactive vitamin B-12, that of the radioactive material presents certain special difficulties. The object is to achieve as high a utilization of the very expensive radioactive cobaltous ion as possible, whereas in the inactive preparation, the degree of utilization of the relatively cheap inactive cobalt is immaterial, and it can, therefore, be present in excess. In practice, the yield, based upon the utilization of the radioactive cobalt, that is, the radiochemical yield, is seldom greater than 20%. A fermentation reaction, with its large volume of fermentation medium and its ensuing tedious stages of isolation of the product, raises particular difficulties in the context of radioactive working as regards radiation protection of the operaters and the spread of radioactive contamination. However, the greatest difficulties are encountered when it is necessary to prepare the radioactive vitamin B-12 at high specific activity.

When employed for the in vivo purposes mentioned above, a specific activity in the region of 1 microcurie of cobalt-57 or of cobalt-58 per microgram of vitamin B-12 is all that is necessary, and this specific activity presents no preparation difficulties other than those already described. For use in saturation analysis methods for the determination of vitamin B-12 levels in blood, specific activities in the region of 200 microcuries of cobalt-57 per microgram of vitamin B-12 are desirable. The highest possible specific activity of a preparation of vitamin B-12 labelled with cobalt-57 is 356 microcuries of cobalt-57 per microgram of vitamin B-12. In practice, it is difficult to prepare cobalt-57 of isotopic abundance greater than 70% (i.e. 70% of the cobalt atoms present are of cobalt-57, and 30% are of inactive cobalt, cobalt-59), and material of this quality would yield vitamin B-12 of specific activity only of about 250 microcuries of cobalt-57 per microgram of vitamin B-12 even if no inactive cobalt were present in the reagents employed in the preparation of the fermentation medium. Some cobalt is inevitably present in the fermentation medium, and it is a matter of extreme difficulty to keep the levels sufficiently low. If, for example, one employs 30mCi of cobalt-57, of 70% isotopic abundance, then if one is to obtain vitamin B-12 of 200 microcuries of cobalt-57 per microgram of vitamin B-12 (that is, of 56% isotopic abundance) the toal amount of cobalt that may be present as an impurity in the fermentation medium is only 1.3 micrograms. Typically, for a preparation on this radioactive scale, 1 liter of a medium containing high concentrations of glucose and of a variety of inorganic salts is employed. When it is realized that the maximum limit of cobalt specified for Analytical Reagent grade distilled water is 500 micrograms per liter, the difficulty of the task of preparing a fermentation medium with such low levels of cobalt will be appreciated, and it is not surprising that a high percentage of production runs fail to yield vitamin B-12 of the desired specific activity.

For these reasons, we have sought to develop a method of production of vitamin B-12, labelled with such radioactive isotopes of cobalt as cobalt-57 cobalt-58, which does not involve the use if the radioactive cobalt in a fermentation reaction.

The invention accordingly provides in one aspect, as a novel material in its own right, vitamin B-12 labelled with cobalt-57, the isotopic abundance of cobalt-57 being sufficient to give the compound a specific activity of at least 250 mCi/mg.

The invention also provides in another aspect a method of making vitamin B-12 which method comprises reacting α-(5,6-dimethylbenzimidazolyl) hydrogenobamide, with cobaltous ion, which cobaltous ion contains an abundance of one or more radioactive isotopes higher than that found naturally, and recovering the labelled vitamin B-12.

α-(5,6-Dimethylbenzimidazolyl) hydrogenobamide is a vitamin B-12 precursor whose molecule is identical with that of vitamin B-12, except that the cobalt atom (and the group which is attached to the cobalt atom in the molecule of vitamin B-12) is missing.

Vitamin B-12 belongs to a class of chemical compounds containing a prophyrin-like structure known as corrin, and the class is known as corrinoids. Toohey (Toohey, J I, Proc Nat Aca Sci, 1965, 54, 934, Fed Proc, 1966, 25, 1628) reported the formation by microorganisms of a number of cobalt-free corrinoids which could be made to incorporate cobalt by reaction with cobaltous chloride, e.g. by heating with 0.01 molar cobaltous chloride and 0.02 molar ammonium hydroxide at 100° for 2 minutes or at 22° for 10 hours. The preparation of a new cobalt-free corrinoid was reported by Koppenhagen, V B and Pfiffner, J J, J Biol Chem, 1971, 246, 3075-3077 who grew Chromation (ATCC 17899) on a medium containing 5,6-dimethylbenzimidazole. This corrinoid was identified as α-(5,6-dimethylbenzimidazolyl) hydrogenobamide. It may be converted to α-(5,6)dimethylbenzimidazole) cobamide cyanide (that is, cyanocobalamin) by treatment with cobaltous chloride and cyanide ion.

Cobalt has an electron configuration such that a cobalt atom in the vitamin B-12 molecule is attached, not only to the corrin ring and to the 5,6-dimethylbenzimidazole, but also to another group. In naturally occurring vitamin B-12, this group may have a variety of identities, including hydroxyl, methyl, and adenosine; in commercial vitamin B-12, the group is usually cyanide, because cyanocobalamin is more stable to storage and transport than hydroxocobalamin. The nature of this group is, however, not critical to the biological activity of the compound. We use the term vitamin B-12 to cover the compounds with various different groups attached to cobalt.

The preferred method for the production of vitamin B-12 labelled with cobalt-57, cobalt-58 and possibly with cobalt-60, involves the isolation and purification of α-(5,6-dimethylbenzimidazolyl) hydrogenobamide followed by its reaction with the corresponding radioactive cobaltous ion under conditions designed to ensure the maximum utilization of the radioactive cobal followed by addition of cyanide ion and separation of the labelled vitamin B-12 from the reaction mixture. The mixture after completion of the reaction is highly complex. In addition to cyanocobalamin and unchanged cobaltous ion it contains a variety of organic compounds containing cobalt-57 resulting from reaction with impurities in the starting material, from decomposition during the course of the reaction, and in certain cases from reaction between the cobalt-57 and the impurities in the solvent. Cobaltous chloride and cobaltous sulphate are suitable starting materials. If the cobalt is present as a complex, this should be one which is readily dissociated to yield the free ion.

If it is desired to obtain the maximum yield of cyanocobalamine, cobalt-57 (based upon utilization of the cobaltous ion, cobalt-57) the vitamin B-12 precursor should be employed in excess. On the other hand, when the highest possible specific activity is required, the cobalt-57 should be employed either in stoichiometric amount or in excess, so as to minimize the contribution from any trace of vitamin B-12 itself (or other forms of cobalt) present as impurities in the vitamin B-12 precursor. In practice, successful preparations have been carried out using ratios of between 50 and 0.2 molecules of vitamin B-12 precursor to each atom of cobalt.

The reaction is preferably performed by treating the vitamin B-12 precursor with cobaltous ion, cobalt-57, in an organic solvent e.g. ethanol or aqueous ethanol, or in an aqueous medium within a broad pH range preferably from 4 to 8 in darkness to minimize decomposition of the vitamin B-12 precursor and of the vitamin B-12 produced. A suitable range of temperature for performance of the reaction is 20° to 80° C.

While the process can be usefully applied with any abundance of a radioactive isotope of cobalt above that found naturally, it is of particular advantage, for reasons explained earlier, with cobalt-57 in an isotopic abundance to provide labelled vitamin B-12 having a specific activity of at least 150 mCi/mg. The radioactive isotope of cobalt employed may, however be cobalt-57, cobalt-58 or cobalt-60 according to need.

The advantages from this new method are:

1. Better yield in terms of radioactive isotope (taking into account the ease of recovery of starting material if this is necessary).

2. A process more easy to adapt to the requirements of radioactive working.

3. No loss of specific activity because of the ease of adequate removal of unwanted cobalt impurities from the small quantities of inactive reagents employed. Any process for labelling vitamin B-12 by exchange of cobalt atoms must inherently involve loss of specific activity.

There follows a discussion of the experimental conditions used for the reaction.

Preparation of the metal-free precursor of vitamin B-12 α-(5,6-dimethylbenzimidazolyl) hydrogenobamide 1. Chromatium (ATCC 17899 and other strains) was grown in the presence of 5,6-dimethylbenzimidazole essentially as described by Koppenhagen V. B. and Pfiffner J. J. (Journal of Biological Chemistry, 1971, 246, 3075-3077). The strains were processed as described below, and the crude products obtained gave closely similar results in experiments on the insertion of radioactive cobalt (Co-57) for the production of Cyanocobalamin Co-57.

2. Quantities of 200 to 300g of the wet cells were processed essentially as described by Koppenhagen V. B. et al. (Journal of Biological Chemistry, 1973, 248, 7999-8002). The crude product contained about 10% of the metal-free precursor of vitamin B-12 as judged spectroscopically by its extinction at 490nm. It was employed without further purification in the work described below.

Insertion of radioactive cobalt (Co-57) into the metal-free precursor of vitamin B-12

3. The crude metal-free vitamin B-12 precursor and cobaltous chloride (Co-57) were dissolved in a variety of solvents (including ethanol, dimethyl sulphoxide and dimethylformamide) and permitted to react, in the dark, for periods varying from a few minutes at 80° C. to several days at room temperature. Insertion of cobalt was shown to take place under all the conditions examined. It proved convenient to employ ethanol as the solvent for the crude metal-free precursor and to add to it cobaltous chloride (Co-57) in a small volume of neutral aqueous solution to give a final solvent composition of 75% to 90% of ethanol. Reaction was allowed to proceed for 48 hours in the dark.

4. In early experiments the cyanocobalamin (Co-57) was recovered by the addition of carrier (non-radioactive) hydroxocobalamin followed by potassium cyanide (to convert hydroxocobalamin to cyanocobalamin). In later experiments, high specific activity cobaltous chloride (Co-57) was employed and the cyanocobalamin (Co-57) was isolated without the addition of carrier.

5. The ratio of metal-free precursor to cobaltous ion (expressed as the number of molecules of metal-free precursor to the number of atoms of cobalt) was varied over a very wide range, the number of molecules of metal-free precursor per atom of cobalt varying from 0.2 to 50.

6. Yields are defined on the basis of the percentage of cobalt-57 incorporated into cyanocobalamin, thus:

actual yield = (a)

$$\frac{\text{activity of Co-57 recovered as cyanocobalamide}}{\text{activity of Co-57 employed as cobaltous ion}}$$

yield (as a percentage of theoretical yield) = (b)

$$\frac{\text{actual yield of cyanocobalamin Co-57}}{\text{the theoretically possible yield of cyanocobalamin, Co-57}}$$

It will be noted that if the metal-free precursor is employed in an amount greater than, or equal to, 1 molecule of metal-free precursor per atom of cobalt, the theoretically possible yield is 100%. But if e.g. 0.5 molecules of metal-free precursor are used per atom of cobalt, the theoretically possible yield is 50%.

7. As would be expected, the best actual yields were obtained when the metal-free precursor was used in excess. Thus a series of 5 experiments was carried out using a 20 fold to 50 fold excess of metal-free precursor in aqueous ethanol at room temperature as previously described. The actual yields varied between 34% and 56% and averaged 51%.

8. In a series of experiments in which between 1 atom and 2 atoms of cobalt were employed per molecule of metal-free precursor, the yields were approximately 10% of the theoretical yield. There were indications that these yields could be improved by a better choice of reaction conditions (e.g. by working at higher temperatures and at higher concentrations).

Isolation of cyanocobalamin (Co-57)

9. A variety of procedures was employed to isolate the cyanocobalamin (Co-57) from the reaction mixture. Typically the reaction mixture was evaporated to dryness under reduced pressure, dissolved in water, and applied to a column packed with polystyrene beads (Amberlite XAD-2). The column was washed with water (to remove inorganic cobalt) and then the cyanocobalamin fraction was eluted with a 20% solution of tert-butanol in water. Final purification was by well established procedures employing cation exchange resin (e.g. Amberlite IR 120) anion exchange resin (e.g. Amberlite IRA 400) carboxymethoxycellulose and DEAE cellulose.

Identification and radiochemical purity of the Cyanocobalamin Co-57

10. Radiochemical purity is the proportion of the Co-57 in the product which is present in the chemical form of cyanocobalamin. The identity and radiochemical purity of the final product was indicated by paper electrophoresis, by thin layer chromatography in several systems (notably silica gel using methanol/water and on cellulose using sec-butanol/water/aceticacid) and by the method described in the British Pharmacopoeia (1973) monograph on Cyanocobalamin ($^{57}$Co). In experiments in which no carrier hydroxo- or cyanocobalamin was added, the identity and chemical purity of the final product was demonstrated by its absorption spectrum as described in the British Pharmacopoeia (1973) monograph on Cyanocobalamin.

Specific activity of the Cyanocobalamin (Co-57)

11. The specific activity (or specific radioactivity) of the final product was determined from its total cobalt-57 content, and from its total cyanocobalamin content as measured spectroscopically as described in the British Pharmacopoeia 1973 monograph on cyanocobalamin.

EXAMPLE 1

In this example a ratio of about 2 molecules of vitamin B-12 precursor is employed per atom of cobalt.

To about 2.5 µg of α-(5,6-dimethylbenzimidazolyl) hydrogenobamide (present in 25 µg of the crude material prepared in sections 1 and 2 above) was added to 3.0 ml of ethanol. A solution of cobaltous chloride Co-57 (0.40 mCi in 0.054 µg of cobalt, corresponding to an isotopic abundance of 82%) in 0.4 ml of water, pH 7.0 to 7.5, was added and the solution was maintained at ambient temperature, in the dark, for 48 hours. Carrier hydroxocobalamin and cyanide ion were added. The crude reaction mixture was divided into two portions and each was evaporated to dryness. The portions were processed by different methods, namely, the use of XAD-2 resin as described above, and extraction of the cyanocobalamin into cresol/carbon tetrachloride 1:1, washing of the organic phase with water, and back-extraction into water by addition of n-butanol/carbon tetrachloride 2:1. Examination of the resulting crude B-12 by electrophoresis in each case indicated a yield of cyanocobalamin in the reaction mixture of 50 to 60% (based upon cobalt-57).

EXAMPLE 2

In this example a ratio of 5 molecules of vitamin B-12 precursor is employed per atom of cobalt.

About 340 µg of α-(5,6,dimethylbenzimidazolyl) hydrogenobamide (present in 3.4 mg of the crude material prepared as in sections 1 and 2 above) was dissolved in 2.0 ml of water to give a cloudy orange pink solution. A solution of cobaltous chloride Co-57 (20mCi of Co-57 in 2.7 µg of cobalt, corresponding to an isotopic abundance of 82%) in 3.0 ml of water, pH 7.0 to 7.5, was added and the solution was maintained in a sealed vessel, in a water bath at 80° C., in the dark, for two hours.

At the end of that time a 5% aliquot of the solution was processed, after addition of hydroxocobalamin carrier and cyanide ion, by passage down an XAD-2 column and elution with 20% tertbutanol in water followed by electrophoresis. The electrophoresis strip contained a number of areas of radioactivity, including a sharp peak corresponding precisely with the narrow pink-coloured band due to cyanocobalamin. From the data obtained, it was calculated that 2.0 mCi of cyanocobalamin, Co-57, was present in the reaction mixture (10% yield on Co-57).

The bulk of the reaction mixture was processed, as described previously, without addition of carrier. Upwards of 1 mCi of cyanocobalamin, Co-57 at 90% radiochemical purity was recovered (50% yield as Co-57). The amount was too small to permit a determination of specific activity, but the calculated specific activity was 300 µCi/µg).

Forms of vitamin B-12 in which the cyanide group is replaced by a hydroxyl or other group can readily be made from cyanocobalamin by known techniques.

Purification of the starting materials by known techniques, give rise to improved results.

We claim:

1. A method of making cyanocobalamin labelled with Cobalt-57, which method comprises providing a reaction mixture containing from 0.2 to 50 molar parts of alpha-(5,6-dimethylbenzimidazolyl)hydrogenobamide and 1 molar part of a cobaltous compound in solution in a solvent which is inert to the reactants, the cobaltous ion of said cobaltous compound containing an abundance of Cobalt-57 higher than that found naturally, effecting reaction therein between the alpha-(5,6-dimethylbenzimidazolyl)hydrogenobamide and the cobaltous ion with the production of hydroxocobalamin,
converting hydroxocobalamin to cyanocobalamin by reaction with excess cyanide ion, and
recovering cyanocobalamin labelled with Cobalt-57.

2. A method according to claim 1 wherein said cyanocobalamin has a specific activity of at least 250 mCi/mg.

3. A method according to claim 1, wherein alpha-(5,6-dimethylbenzimidazolyl)hydrogenobamide is reacted with cobaltous chloride or cobaltous sulphate in an aqueous or aqueous alcoholic medium.

4. A method according to claim 1, wherein reaction is effected by heating the reactants in darkness in an aqueous or aqueous alcoholic medium at a pH of from 4 to 8.

5. Vitamin B-12 having a specific activity of at least 250 mCi/mg. which has been labelled with Cobalt-57 by reacting alpha-(5,6-dimethylbenzimidazolyl)hydrogenobamide with a cobaltous compound.

6. Cyanocobalamine having a specific activity of at least 250 mCi/mg. which has been labelled with Cobalt-57 by a method comprising the steps of:
providing a reaction mixture containing from 0.2 to 50 molar parts of alpha-(5,6-dimethylbenzimidazolyl) hydrogenobamide and 1 molar part of a cobaltous compound in solution in a solvent which is inert to the reactants, the cobaltous ion of said cotaltous compound containing an abundance of Cobalt-57 higher than that found naturally,
effecting reaction therein between the alpha-(5,6-dimethylbenzimidazolyl)hydrogenobamide and the cobaltous ion with the production of hydroxocobalamin,
converting hydroxocobalamin to cyanocobalamin by reaction with excess cyanide ion, and
recovering cyanocobalamin labelled with Cobalt-57 and having the above activity.

* * * * *